US012596575B2

(12) United States Patent
Etemadi et al.

(10) Patent No.: US 12,596,575 B2
(45) Date of Patent: Apr. 7, 2026

(54) DATA STREAMING PIPELINE FOR COMPUTE MAPPING SYSTEMS AND APPLICATIONS

(71) Applicant: Northwestern Memorial HealthCare, Chicago, IL (US)

(72) Inventors: Mozziyar Etemadi, Chicago, IL (US); Stacey Caron, Chicago, IL (US); Aditya Sharma, Chicago, IL (US); James Heller, Chicago, IL (US); Caitlin Teague, Chicago, IL (US); Vladislav Mukhin, Chicago, IL (US); Galal Galal, Chicago, IL (US); Matthew Wittbrodt, Chicago, IL (US); Matthew Klug, Chicago, IL (US); Albert Kim, Austin, TX (US); Priyanka Soni, Pune (IN); Pradeep Sama, Chicago, IL (US); Faraz Ahmad, River Forest, IL (US)

(73) Assignee: Northwestern Memorial Healthcare, Chicago, IL (US)

( * ) Notice: Subject to any disclaimer, the term of this patent is extended or adjusted under 35 U.S.C. 154(b) by 608 days.

(21) Appl. No.: 18/158,824

(22) Filed: Jan. 24, 2023

(65) Prior Publication Data
US 2023/0236886 A1 Jul. 27, 2023

Related U.S. Application Data

(60) Provisional application No. 63/302,798, filed on Jan. 25, 2022, provisional application No. 63/302,811, (Continued)

(51) Int. Cl.
G06F 9/50 (2006.01)
G16H 10/60 (2018.01)

(52) U.S. Cl.
CPC ........... G06F 9/5005 (2013.01); G16H 10/60 (2018.01)

(58) Field of Classification Search
None
See application file for complete search history.

(56) References Cited

U.S. PATENT DOCUMENTS 11,315,041 B1 * 4/2022 Jain ........................ G06N 20/20
2010/0099974 A1 4/2010 Desai
(Continued)

FOREIGN PATENT DOCUMENTS

WO 2017152121 A1 9/2017
WO WO-2022033706 A1 * 2/2022 ............. G16H 50/20

OTHER PUBLICATIONS

R. Aurangzaib, W. Iqbal, M. Abdullah, F. Bukhari, F. Ullah and A. Erradi, "Scalable Containerized Pipeline for Real-time Big Data Analytics," 2022 IEEE International Conference on Cloud Computing Technology and Science (CloudCom), Bangkok, Thailand, 2022, pp. 25-32. (Year: 2022).*
(Continued)

*Primary Examiner* — Frank D Mills
(74) *Attorney, Agent, or Firm* — Hogan Lovells US LLP

(57) ABSTRACT

Approaches presented herein provide systems and methods for a data platform to identify, evaluate, and map data for processing via one or more compute instances. The data platform may receive an instruction and retrieve data from a variety of remote data locations. The data may be processed, such as to label or file the data, and then streamed to a compute instance for further evaluation. The data platform may be used to provide a centralized system for managing system data that combine both legacy and modern storage solutions into a single integrated platform.

19 Claims, 9 Drawing Sheets

Related U.S. Application Data filed on Jan. 25, 2022, provisional application No. 63/302,807, filed on Jan. 25, 2022.

(56) References Cited

U.S. PATENT DOCUMENTS

| | | | |
|---|---|---|---|
| 2016/0350919 A1 | 12/2016 | Steigauf | |
| 2018/0055468 A1 | 3/2018 | Reicher | |
| 2019/0088359 A1 | 3/2019 | Moore | |
| 2020/0027210 A1* | 1/2020 | Haemel | G06F 9/5038 |
| 2020/0211692 A1 | 7/2020 | Kalafut | |
| 2020/0250336 A1 | 8/2020 | Stockert | |
| 2020/0321101 A1 | 10/2020 | Karargyris et al. | |
| 2020/0349434 A1 | 11/2020 | Zhang | |
| 2021/0098133 A1 | 4/2021 | Chowdhry et al. | |
| 2021/0216822 A1 | 7/2021 | Palik | |
| 2021/0225512 A1 | 7/2021 | Himeno | |
| 2021/0228276 A1 | 7/2021 | Giraldez | |
| 2022/0051114 A1 | 2/2022 | Lyman | |
| 2023/0145236 A1* | 5/2023 | Bagnell | B60W 60/0011 701/25 |
| 2024/0232594 A1* | 7/2024 | Yang | G06N 3/063 |

OTHER PUBLICATIONS

International Search Report of PCT/US2023/061274, mailed May 11, 2023.

Akshay Arora, et. al., "ISTHMUS: Secure, Scalable, Real-time and Robust Machine Learning Platform for Healthcare", Parkland Center for Clinical Innovation, (2019), pp. 1-11.

GE Healthcare "Marquette 12SL Algorithm Connected Clinical Excellence", General electric Company (2016), 10 pgs.

"Second Opinion—Real-Time Pathology Detection Aid for Denists, from Dentistry's Global AI Leader", Pearl, Inc. (2021) 4 pages Second Opinion—Real-time pathology detection aid for dentists, from dentistry's global AI leader (hellopearl.com).

RadLogics, Inc.—515599—Apr. 5, 2018 | FDA—FDA Warning Letter—Apr. 5, 2018.

Akshay Arora, et. al., "ISTHMUS: Secure, Scalable, Real-time and Robust Machine Learning Platform for Healthcare", Parkland Center for Clinical Innovation, Oct. 1, 2019, pp. 1-11, arXiv:1909.13343v2.

* cited by examiner

Figure 1:
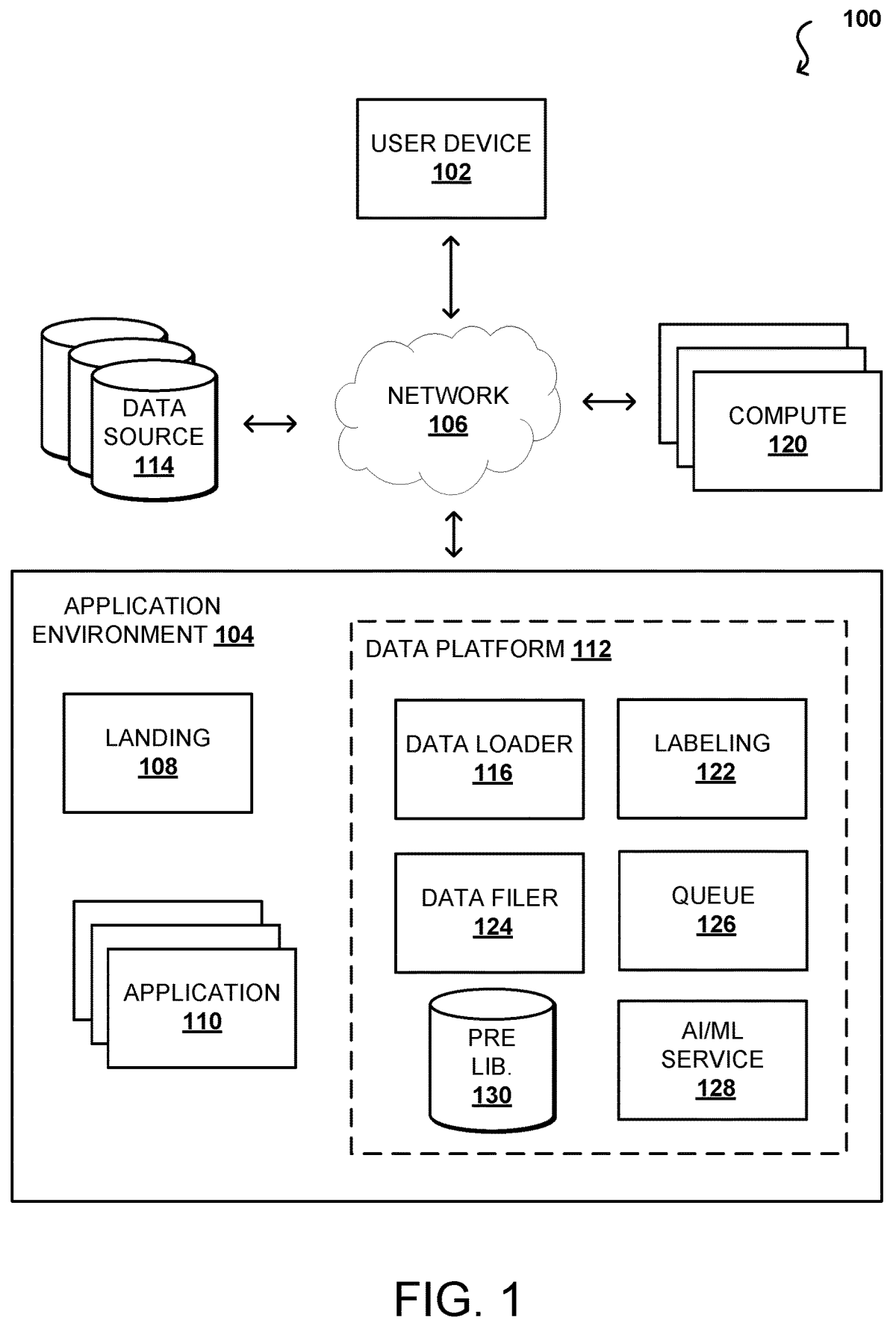

100

USER DEVICE
102

DATA SOURCE
114

NETWORK
106

COMPUTE
120

APPLICATION ENVIRONMENT 104

DATA PLATFORM 112

LANDING
108

APPLICATION
110

DATA LOADER
116

LABELING
122

DATA FILER
124

QUEUE
126

PRE LIB.
130

AI/ML SERVICE
128

DATA SOURCE 114

DATA FILER 120

CONFIG 302

AI/ML PIPELINE 304

ALERT 306

PROCESSING 308

320

PRE LIB. 130

CONFIG 322

DATA SOURCE 114

COMPUTE 120

QUEUE 126

OUTPUT 324

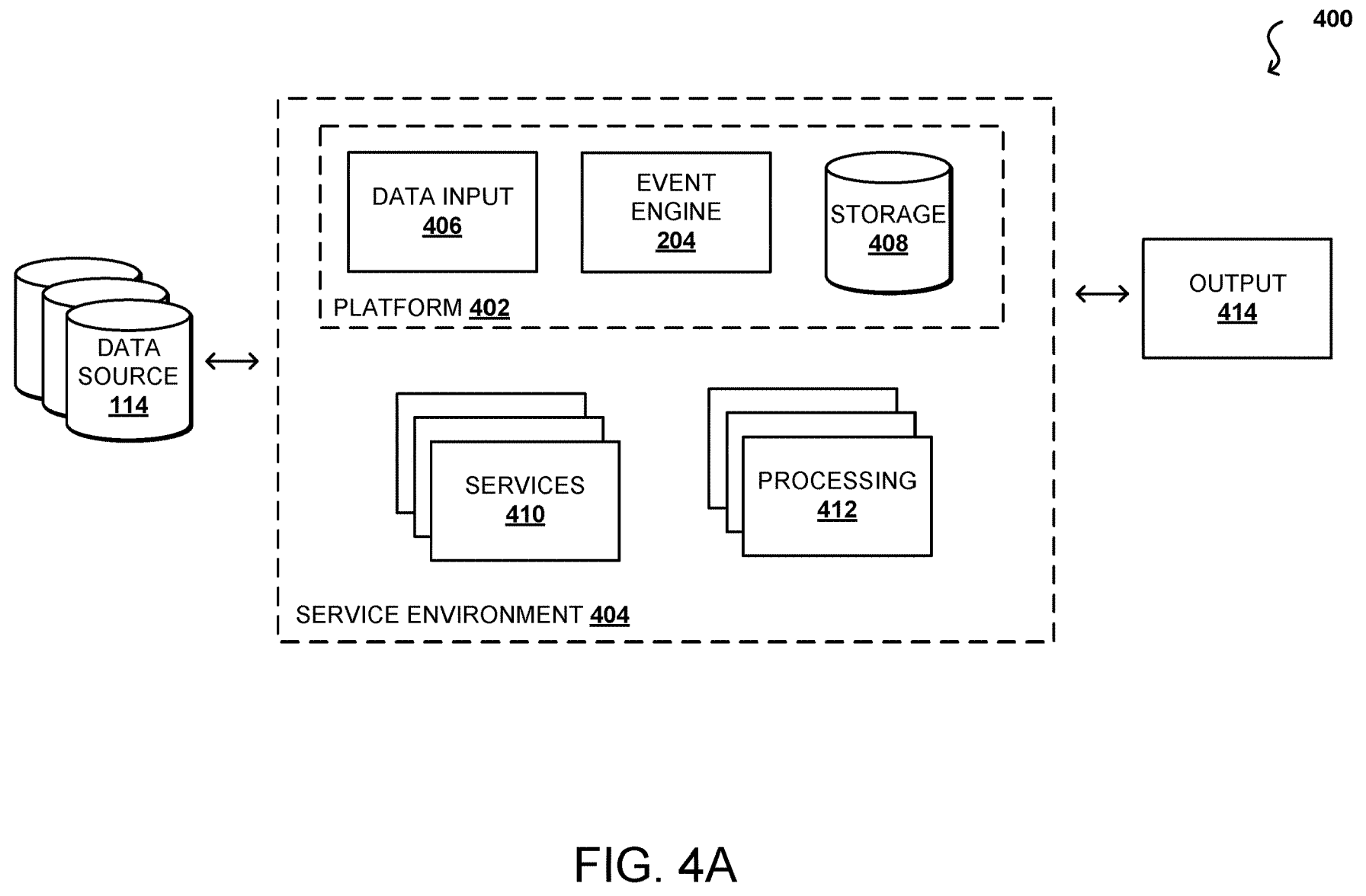

400

OUTPUT 414

SERVICE ENVIRONMENT 404

PLATFORM 402

DATA INPUT 406

EVENT ENGINE 204

STORAGE 408

SERVICES 410

PROCESSING 412

DATA SOURCE 114

FIG. 4A

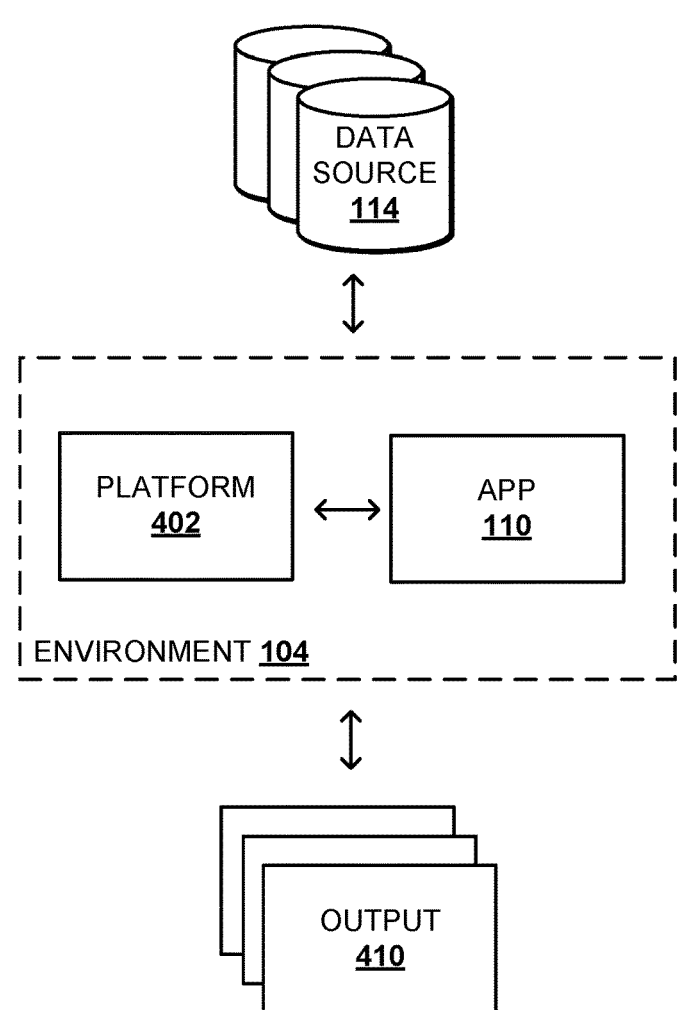
FIG. 4B

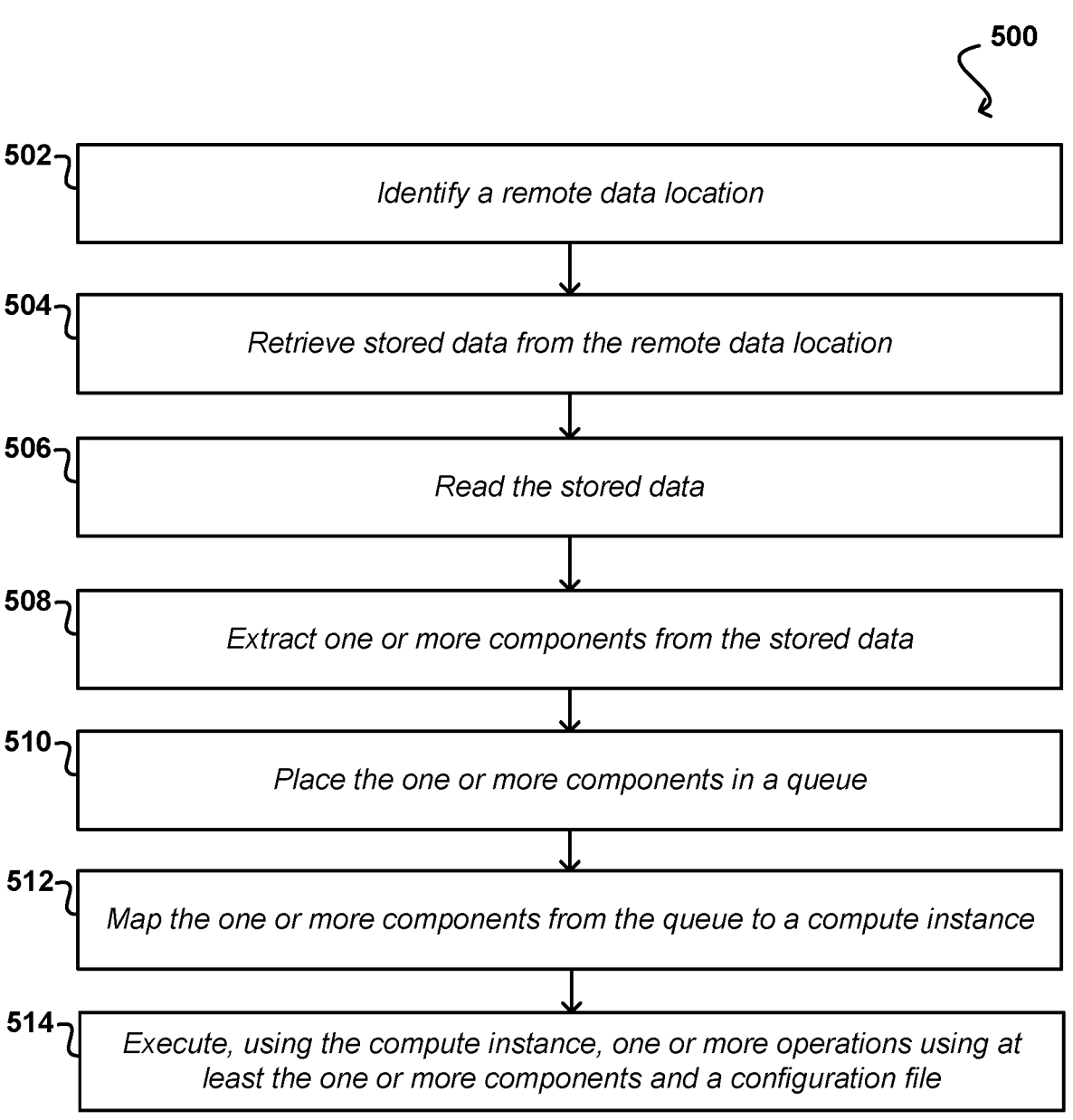

500

502 — Identify a remote data location

504 — Retrieve stored data from the remote data location

506 — Read the stored data

508 — Extract one or more components from the stored data

510 — Place the one or more components in a queue

512 — Map the one or more components from the queue to a compute instance

514 — Execute, using the compute instance, one or more operations using at least the one or more components and a configuration file

FIG. 5A

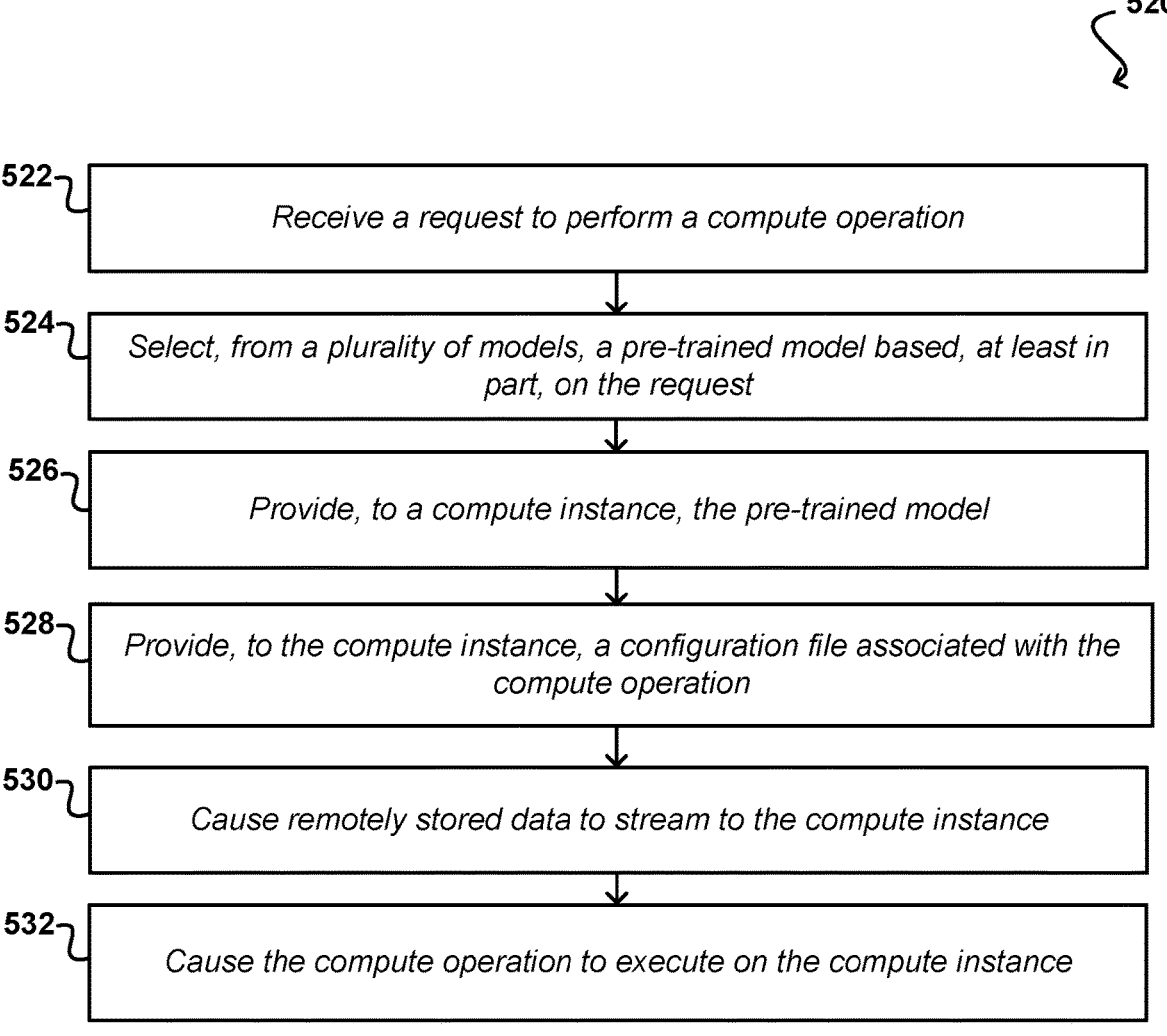

520

522 — Receive a request to perform a compute operation

524 — Select, from a plurality of models, a pre-trained model based, at least in part, on the request 526 — Provide, to a compute instance, the pre-trained model 528 — Provide, to the compute instance, a configuration file associated with the compute operation 530 — Cause remotely stored data to stream to the compute instance 532 — Cause the compute operation to execute on the compute instance

FIG. 5B

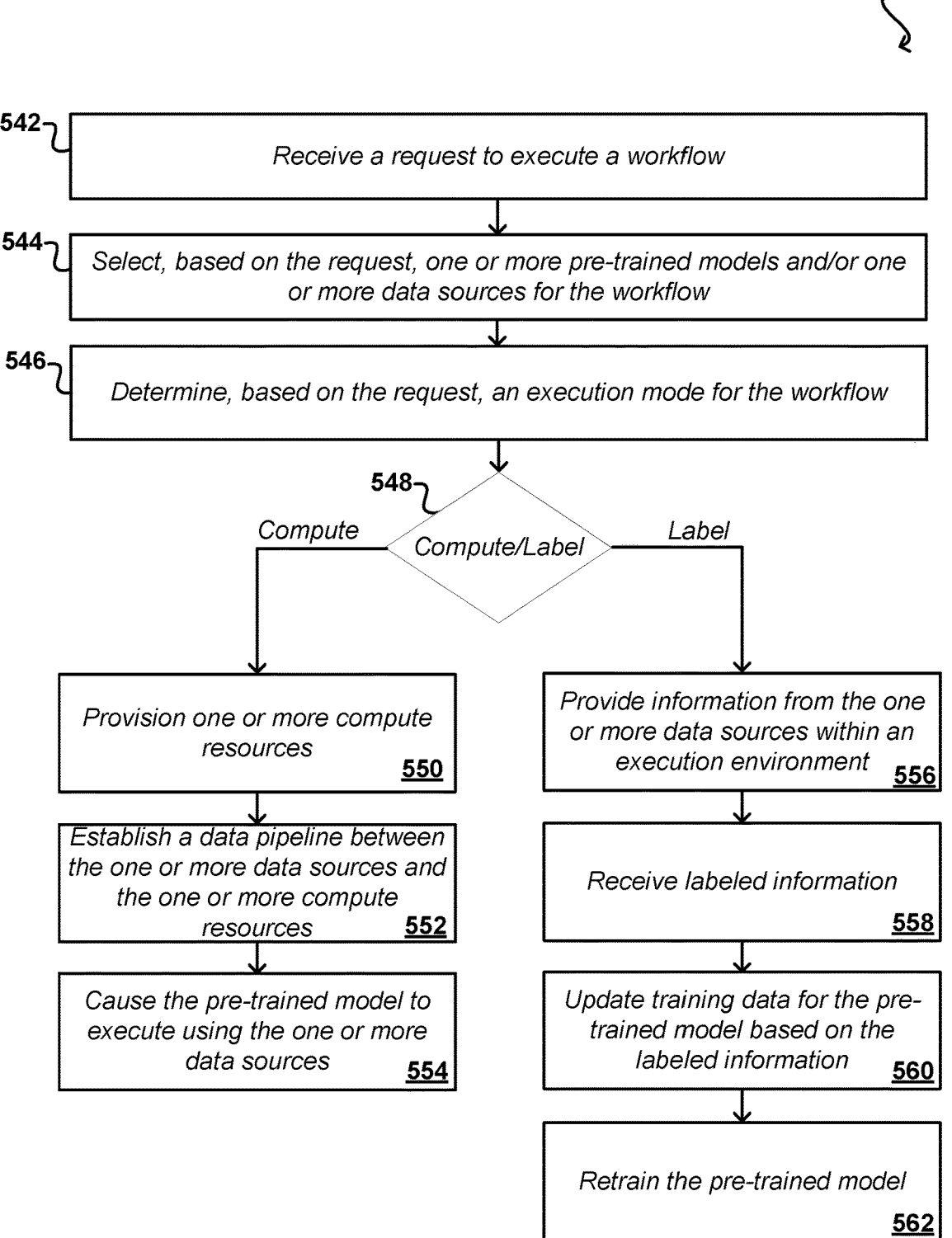

540

542 — Receive a request to execute a workflow

544 — Select, based on the request, one or more pre-trained models and/or one or more data sources for the workflow 546 — Determine, based on the request, an execution mode for the workflow 548 — Compute/Label Compute Label Provision one or more compute resources 550

Establish a data pipeline between the one or more data sources and the one or more compute resources 552

Cause the pre-trained model to execute using the one or more data sources 554

Provide information from the one or more data sources within an execution environment 556

Receive labeled information 558

Update training data for the pre-trained model based on the labeled information 560

Retrain the pre-trained model 562

FIG. 5C

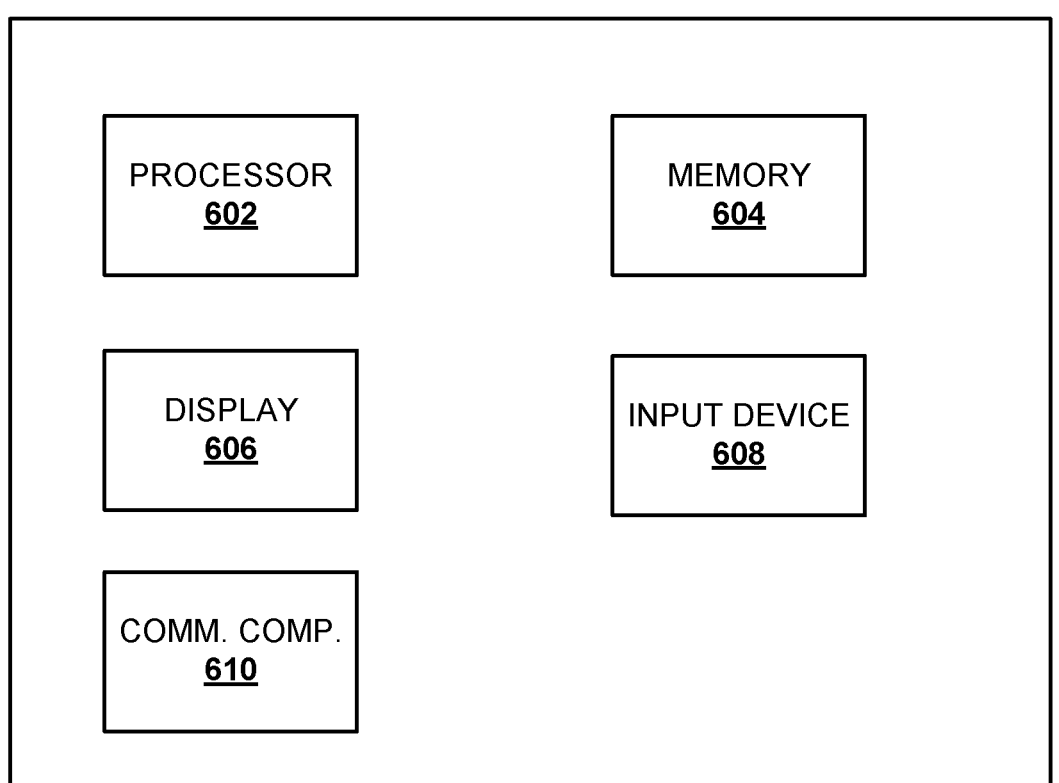
FIG. 6

DATA STREAMING PIPELINE FOR COMPUTE MAPPING SYSTEMS AND APPLICATIONS

CROSS-REFERENCE TO RELATED APPLICATIONS

This application claims priority to and the benefit of U.S. Provisional Patent Application No. 63/302,798, filed Jan. 25, 2022, titled "MULTIMODAL CARDIOVASCULAR DISEASE DETECTION AND RISK PREVENTION," U.S. Provisional Patent Application No. 63/302,807, filed Jan. 25, 2022, titled "PRETRAINED BASE MODELS," and U.S. Provisional Patent Application No. 63/302,811, filed Jan. 25, 2022, titled "DATA PLATFORM," the full disclosures of which are hereby incorporated in their entireties for all purposes.

BACKGROUND

Accessing and using vast quantities of data may present several challenges due to the way the data is stored, filed, or transmitted. For example, data that is stored at remote locations may be difficult to obtain for meaningful analysis and evaluation without expending significant resources for data transmission and local storage. Additionally, when looking at data from multiple different users within a single organization, different filing and storage procedures may cause difficulties with respect to identifying, organizing, and preparing data for processing. Additionally, transmission of vast quantities of data is time consuming and costly.

BRIEF DESCRIPTION OF THE DRAWINGS

Various embodiments in accordance with the present disclosure will be described with reference to the drawings, in which:

FIG. 1 illustrates an example environment for a data platform, in accordance with various embodiments;

FIG. 4A illustrates an example service environment, in accordance with various embodiments;

FIG. 4B illustrates an example digital health platform, in accordance with various embodiments;

FIG. 5A illustrates an example process for executing a compute operate using remote data, in accordance with various embodiments;

FIG. 5B illustrates an example process for executing a compute operating with a pre-trained model, in accordance with various embodiments;

FIG. 5C illustrates an example process for determining and provisioning different execution modes for a workflow, in accordance with various embodiments; and FIG. 6 illustrates a computer system, according to at least one embodiment.

DETAILED DESCRIPTION

Figure 2:
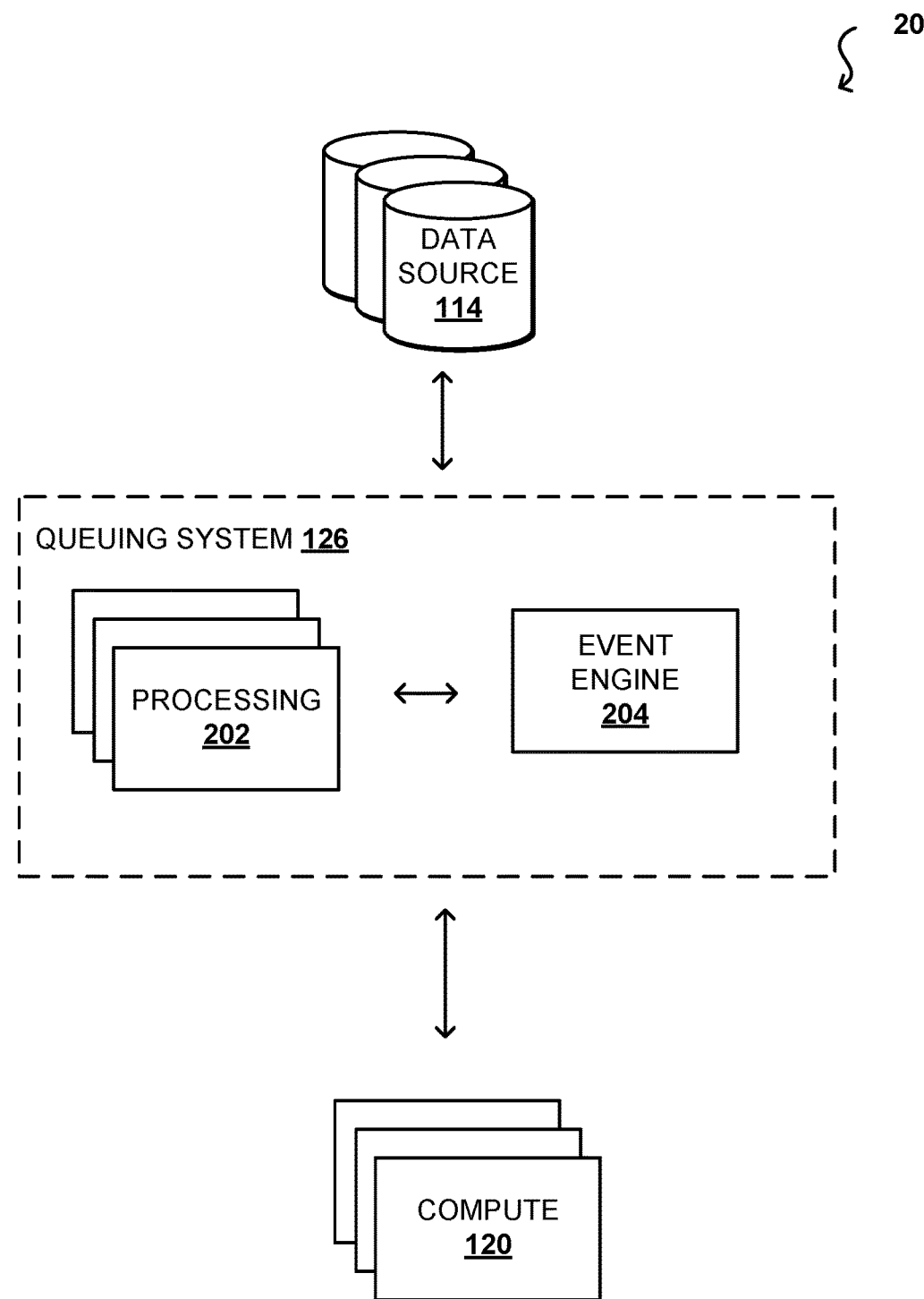
FIG. 2 illustrates an example environment of a queuing system in use with a compute service, in accordance with various embodiments.

In the following description, various embodiments will be described. For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiment being described.

Approaches in accordance with various embodiments leverage a data pipeline to permit streaming and direct mapping of a variety of data resources to one or more compute services, such as directly to a graphics processing unit (GPU). Embodiments of the present disclosure may relate to a platform to use artificial intelligence (AI) and/or machine learning (ML) to process information using one or more pre-trained models that are updated and/or configured based on one or more configuration files for a desired task. In this manner, a collection of data may be used as input to a variety of different AI/ML applications in an enterprise environment. Various embodiments may further incorporate a data platform to enable users to identify data sources, select from the pre-trained models, and establish compute pipelines and/or workflows for processing different types of information. This data platform may be integrated with and/or communicate with the data pipeline to permit efficient data streaming, pre-processing, and mapping along with one or more compute services. In at least one embodiment, specific applications may be deployed with a particular emphasis as defined, at least in part, by one or more configuration files. The data platform may be used to build components of the specific applications and link the data pipeline for data streaming and compute services, thereby enabling sub-systems to be developed within a larger data environment.

Various embodiments are directed toward an integrated platform that may be used to retrieve data from a source via a streaming connection, label the data for filing, provide resources for users to interact with the platform, and to store and/or prepare a library of pre-trained models that may be used for one or more application based on a set of input configuration files. The integrated platform may be used in a variety of industries, such as healthcare, where unique challenges are present with respect to control of information, labeling of data, and the like. For example, electronic health records (EHRs) may be subject to one or more controls with respect to viewing, storing, and distributing the information within the EHRs. Furthermore, in at least one embodiment, EHRs may be present from a variety of different practices or sources, and as a result, data may be coded differently or otherwise difficult to group together. Systems and methods may be used to pre-process information acquired from data sources, such as EHR data sources. This information may then be distributed through one or more pipelines or workflows for processing, such as for filing, for evaluation via one or more compute services, and/or the like. Accordingly, systems and methods may be used to establish an integrated platform to permit one or more users to aggregate data from a variety of sources, prepare the data, transmit the data for use via one or more compute services, and to output results for further action and/or the like.

In at least one embodiment, systems and methods of the present disclosure may incorporate sub-systems directed toward at least engineering/infrastructure, integrated clinical labeling, democratization, and a library of pretrained models. Systems and methods may be used to leverage infrastructure to build a library of pretrained base models to enable clinical and research partners to utilize the platform for various projects. The pre-trained models may be used with various different modalities, including at least multimodal, graph (FHIR), language, image, video, and audio.

Pre-training may increase performance, reduce label requirements, and reduce model development time. A variety of different languages may be implemented to develop the environment, with one or more APIs being deployed to enable communication between systems having different underlying language definitions and/or different storage or compute parameters. In at least one embodiment, systems and methods may include various just-in-time data loaders to both on prem and off prem (e.g., cloud storage) in order to stream data directly into the compute infrastructure. Further embodiment may include a library of APIs that allow for full connectivity to/from a composite of clinical systems, such as EHR for applications in the health field. EHR embeddings and workflow-integrated labeling solutions may also be implemented. Democratization efforts may include standardizing tutorials for model development, deployment, and monitoring.

In at least one embodiment, systems and methods of the present disclosure enable rapid and seamless creation and destruction of ephemeral compute services to facilitate execution of one or more compute operations in accordance with instructions associated with one or more workflows. For example, a workflow may be associated with various machine learning systems, such as those that may process, evaluate, and classify information within an input. Upon execution of the workflow, a compute node may be provisioned to load one or more machine learning applications from a database of pre-trained models, execute commands in accordance with the workflow, and then destroy or otherwise close the node upon completion of the task. In at least one embodiment, creation of compute nodes may be skipped, for example, in embodiments where operations are executed on a local machine, among other options. Systems and methods may enable clinical personnel, such as those that are not intimately familiar with different machine learning systems, to execute applications within the workflow, label information (in certain embodiments), and the like. For example, for clinical personnel that routinely evaluate different patient information, such as imaging information, labeling may be substantially in line with the clinical personnel's skill set in executing their traditional job function, but now, the labeling may be used to facilitate further development of different machine learning systems. Accordingly, clinical personnel may be more intimately involved with the machine learning applications, even when their expertise or particular job function is not directly involved with these systems. As a result, additional expertise may be added to a pool of users due to the decreased barrier to entry.

Various systems and methods further provide a library of pretrained models, which may also be bespoke models that are particularly trained for one or more tasks. By way of example only, a classifier may be particularly trained to identify nodes within lung image information. As another example, a natural language processing system may be particularly trained to identify clinical notes or evaluations within a corpus of text. Systems and methods provide the collection of pretrained libraries, which may then be initialized using one or more configuration files, to enable clinical personnel to either run workflows on their own and/or to facilitate with training of different systems for one or more tasks by providing labeled ground truth information. In various embodiments, use of remote compute systems may enable operation of these models on hardware with reduced computing capacity (compared to data centers, for example) such as smart phones, personal computers, and the like.

Systems and methods also provide for a just-in-time approach for connecting to, identify, and receiving information from one or more different remote data sources. For example, a data pipeline may be established in which selected data is directly mapped to and/or loaded to particular layers of the machine learning system. As a result, the selected data may remain in its storage location within transmitting the data to the compute node and/or device executing the operations. Such systems may also be integrated into various other applications, including enterprise migrations, consolidation of storage, and the like.

Various other such functions can be used as well within the scope of the various embodiments as would be apparent to one of ordinary skill in the art in light of the teachings and suggestions contained herein.

FIG. 1 illustrates an environment 100 in which various embodiments may be deployed. In this example, a user device 102 may be used to communicate with an application environment 104 over a network 106. The user device 102 may be operated by a human user or may be a device that executes instructions, such as a device that is programmed to perform one or more tasks, such as on a continuing or recurring basis. The user device 102 may include one or more electronic devices, such as a computer, smart phone, wearable device, gaming console, server, compute cluster of various processing units, and the like. In at least one embodiment, the user device 102 communicates over the network 106, such as the Internet, in order to interact with the application environment 104. The application environment 104 may be a distributed computing environment (e.g., a "cloud" environment) using a server-based or serverless architecture. In at least one embodiment, the application environment 104 executes on hardware that may be remotely positioned from the user device 102 and may be shared or otherwise used with other systems. For example, one or more components of the application environment 104 may execute on a virtual machine that uses underlying hardware that executes one or more additional virtual machines.

In this example, various modules or sub-systems of the application environment 104 are shown separately for convenience and clarity, but may be integrated into a common module and/or set of programming instructions. For example, operations to label and file data may be integrated into a common platform or application. Various embodiments include a landing environment 108 that may serve as a landing page or introduction to the user device 102. For example, the landing environment 108 may include one or more features to verify access credentials of the user device 102 and/or to provide access in accordance with various user preferences or stored settings. Various applications 110 may also execute within the application environment 104. In at least one embodiment, the application environment 104 may be used to establish one or more workflows to execute within the applications 110. As an example in the medical industry, a first application may be related to evaluating lung imaging data, a second application may be related to evaluating brain imaging data, a third application may be related to evaluating colon imaging data, a fourth application may be related to evaluating contraindications between users with one or more known conditions, and so forth. The applications may be built and executed within an established workflow of the application environment 106, as described herein.

In at least one embodiment, a data platform 112 may execute within the application environment 104 in order to identify, pull, and/or process data from one or more data sources 114, which may be remote data sources. In at least one embodiment, the data platform 112 enables a pipeline for streaming data transmission without moving the data to a new storage location. For example, returning to the example of the medical industry, certain health systems may have large quantities of data that are stored at various locations and associated with different divisions of the health system. This data may include a significant quantity of information that can be processed to improve diagnostics or care for users of the health system. However, with large quantities of data, it may be difficult, time-consuming, and expensive to move the data. Furthermore, with legacy systems, modifying data storage locations could inadvertently change metadata characteristics and/or corrupt certain types of data files. To address these and other drawbacks, systems and methods of the present disclosure enable streaming data from the one or more data sources 114 through a pipeline while maintaining/leaving the data at its present storage location. As a result, the application environment 104 is not burdened with the additional requirement of providing storage locations for the data and also may receive, evaluate, and then direct data to particular locations without intermediate storage. In this manner, information can be queued and then mapped directly to a compute location.

As shown in FIG. 1, the data platform may include a data loader 116 to communicate with one or more data sources 114, for example via the network 106. The data loader 116 may identify specific classes or types of information or identify a storage location, and then establish a pipeline for transmission of information over the network 106. As noted, transmission may be in the form of streaming information and not a wholesale movement or copying of the data, which may lead to reduced bandwidth use. For example, in at least one embodiment, a pipeline may be established in which one or more configuration files may be used to identify files, identify a file location, read information from the file, extract one or more portions of the information, process the data for use with one or more systems of the application environment 104, and the transmit the information to one or more queues, which may be used to map information directly to one or more compute services 120. As noted, these compute services 120 may be provisioned and executed upon a request from the user device 102, as part of a pre-determined workflow, or combinations thereof. In at least one embodiment, information from the one or more data sources 114 may be evaluated, extracted, pre-processed, and then mapped and transmitted directly to one or more compute services, such as to a specific GPU and/or to a specific layer of a trained machine learning system, without moving or otherwise transmitting the data to an intermediate location.

Various embodiments of the present disclosure may also incorporate a labeling system 122, a data filer 124, and/or a queueing system 126. As noted, these systems are shown as separate blocks in the example of FIG. 1, but it should be appreciated that the functionality of these systems may be incorporated into a single component and/or a single platform executing within the application environment 104. In at least one embodiment, the labeling system 122 may be referred to as a unified labeling platform that may be used to consistently label and/or identify data that is used within the application environment 104. For example, legacy data (e.g., data stored with previous labeling instructions or coding instructions) may be rich in information, but such information may be hard to identify and extract when labeled or otherwise buried within other information. Embodiments may be used to extract information from various data sources and to re-label or otherwise improve labeling of the data. For example, an application may execute to scan information within the data and to identify keywords and/or locations of the information. By way of non-limiting example, a document may include information such as a patient location, coding instructions for care, notes regarding health history, and treatment notes. The labeling system 122 may be used to extract information from the treatment notes, for example, to identify whether certain medications were prescribed, certain treatment options were prescribed, and/or the like. While the labeling system 122 is described in various embodiments as an automated system, in at least one embodiment, the labeling system 122 may also be integrated with, or receive information from, a human labeling system. For example, a user may assist the labeling system 122 by identifying data. As will be appreciated, in at least one embodiment, the data loader 116 and/or the labeling system 122 may obscure or otherwise remove identifying information within the data in accordance with various retention and privacy regulations.

The illustrated data filer 124 may direct or otherwise queue information from the obtained data into the queueing system 126. For example, the data filer 124 may identify particular data associated with cardiovascular disease and then direct that information into the queuing system 126 for computation with other indicators for cardiovascular disease. Such a process may be used to develop a workflow that enable large quantities of data to be evaluated, labeled, and then filed into an appropriate location for further processing. It should be appreciated that the data filer 124 may also be used to provide notifications for users of the system. For example, if the labeling system 122 identifies one or more follow up actions, the data filer 124 may be used to provide the information to a notification system to provide an alert or a recommendation for action to a care provider, among other options.

In one or more embodiments, the data filer 124 may be incorporated within one or more orchestration environments as a batch process. As a result, the system may be executed in the background or at certain designated times with limited human interaction. For example, a document repository that includes EHR may be processed to identify information relevant for a particular application. Information may be processed in accordance with one or more configuration files to identify and extract relevant information for a particular application and then loaded into the queueing system 126 for further processing at a later time, for example, when a user returns and provides a configuration file to a pre-trained machine learning system to process the information. In this manner, data can be scanned, evaluated, tagged, and pre-processed with limited human interaction within a pipeline or workflow while the data remains at a first physical location.

The illustrated queueing system 126 may be used to map or otherwise coordinate operation with one or more artificial intelligence (AI) and/or machine learning (ML) services 128. That is, the queueing system 126 may be used to map and/or direct information directly into one or more data iterations of the AI/ML applications executing as part of the service 128. In at least one embodiment, the AI/ML service 128 may use one or more pre-trained models from a pre-trained library 130. For example, the pre-trained libraries may be trained to perform one or more tasks (e.g., classification, image segmentation, data extraction, natural language processing, etc.) in accordance with one or more parameters. The parameters may be provided as part of a configuration file that is particularized with use for a given application. For example, while a pre-trained classifier may be used in classifying both brain imaging data and lung imaging data, embodiments may incorporate different configuration files to identify which features may be associated with a desired output. Additionally, in at least one embodiment, the pre-trained models may be updated and/or modified over periods of time. For example, as new information is acquired through running the AI/MI service 128, such information may be fed back to various models of the pre-trained library 130. Furthermore, new models may be generated as new information is acquired, with those new models being added to the library 130. In this manner, bespoke models may be generated for particular functions (e.g., classification for particular organs, natural language processing for certain types of records, etc.).

Various embodiments of the present disclosure may be used with one or more distributed computing platforms that enables the application environment 104 and/or one or more components of the application environment 104 to integrate with or run alongside the distributed computing platform. For example, the distributed computing platform may provide the one or more compute services 120 based on instructions from the AI/ML service 128 that may load the pre-trained models and configuration information into the compute service 120 for execution. Furthermore, various embodiments may also leverage or otherwise use information or services from the distributed computing platform, such as encryption services, data collection services, metrics collection, and/or the like. Accordingly, various embodiments provide a unified platform in which one or more organizations can share information, even legacy information, to collect, identify, extract, and prepare information for further evaluation or filing, even if information is stored or otherwise coded using different systems.

In at least one embodiment, systems and methods may incorporate a singular location or platform for system-wide data loading, data labeling, and data queuing efforts. Additionally, particular features associated with the functionality of the platform may also be integrated into the platform. For example, characteristics of processing and using EHR may be built into one or more workflows to effectively manage data. The incorporation of a singular management and/or labeling solution may enable a more diverse group of input data. Furthermore, a digital platform for practitioners may enable more users to leverage and use the various applications within the system. Additionally, as noted above, various compute services may be used with pre-trained models. For example, containerized, ephemeral development environments may be connected to spot compute nodes. Furthermore, highly optimized and parallelized just-in-time data loaders may be incorporated to stream cloud and on premises data directly into GPUs. By using a variety of different potential compute resources, which may use a "bring your own model" system, users may gain access to an a la carte menu of highly configurable spot compute resources that reduce costs for end users. Various embodiments may also incorporate tutorials and information for users to learn how to build their own applications and build out custom workflows for their own particular uses. These workflows may also incorporate a library of pre-trained models, as noted herein, that reduces the need for individual and/or additional labeling, increases model performance, reduce modeling time, and allows greater diversity in use cases.

FIG. 2 illustrates an example architecture diagram 200 for a streaming solution that may be associated with one or more embodiments of the present disclosure. In this example, the diagram 200 shows information transmitted from the data sources 114 to the queuing system 126, which incorporates one or more processing systems 202 and an event engine 204. As noted herein, the queuing system 126 may be integrated into one or more additional applications and/or may communicate with other applications to provide different functionality.

The data sources 114 may be transmitted over a network, such as the internet, and may include both remote and on-prem data sources. In at least one embodiment, the on-prem data sources may be hard-wired to one or more compute systems that permit data transmission over a physical connection, such as a universal serial bus. However, it should be appreciated that transmission may also be over a common network or the like. For example, for both remote and on-prem storage, transmission may occur via one or more network connections. The data sources 114 may be associated with a variety of entities, such as different hospital systems within a health network, different departments within a government health system, research information for one or more universities or private institutions, and/or the like. As noted, the way information is stored or maintained may be different between the data sources 114 and/or within the data sources 114. For example, legacy data may be stored differently than newly acquired data. Furthermore, different departments may have different data storage requirements or procedures. Accordingly, various embodiments may implement one or more processing systems 202, which may be batch processing systems, to receive, evaluate, extract, and/or label different data from the data sources 114. In at least one embodiment, multiple processes may be used. For example, for text-only information, a single processing step may be sufficient to extract relevant information. However, for multimodal information, such as data that includes both text and images or text, images, and video, multiple processing steps may be used. As a result, data may be converted from raw or substantially raw data to processed or pre-processed data. The conversion between data types may include eliminating extraneous information, anonymizing data, extracting salient information, and/or the like.

In various embodiments, the event engine 204 may be implemented to monitor different steps of the queuing process and to prepare information for mapping to one or more compute services 120. For example, the event engine 204 may control a number of queues that are open, control topics within queues, manage subscriptions, and the like. Furthermore, the event engine may direct data for processing based on data modalities, expected output sources, and the like. For example, if a configure file provides information that data will be used in natural language processing, one step of the processing may include removal of images or graphics from the documents, as these portions may increase a document size and will not be evaluated at the compute service 120.

The event engine 204, as part of or separate from the queuing system 126, may be used to map or otherwise direct information (e.g., processed data, raw data, etc.) to one or more compute services 120. The data may be mapped directly to a GPU and streamed to the GPU without requiring movement from the original storage location. In this manner, particular information may be extracted and used with various compute services without copying data over. Furthermore, data from a variety of sources 114 may be collected, processed, and then integrated into different pipelines and workflows for analysis.

Figures 3A, 3B:
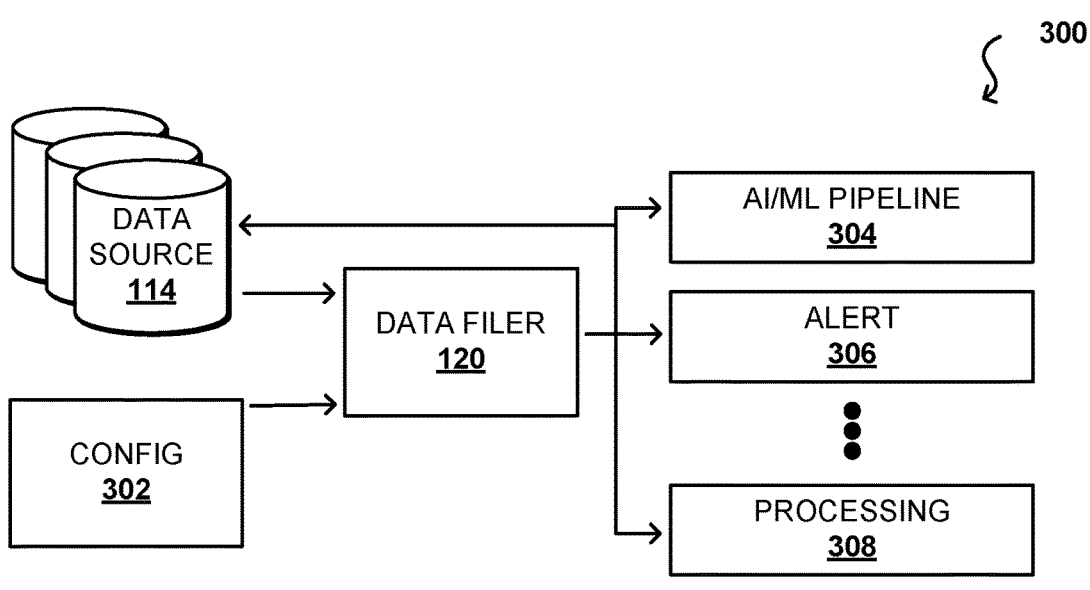
FIG. 3A illustrates an example environment of a data filer, in accordance with various embodiments.
FIG. 3B illustrates an example environment of a compute service, in accordance with various embodiments.

FIG. 3A illustrates a data sorting environment 300 that may be used with embodiments of the present disclosure. In this example, the data filer 124 is illustrated as a system to receive information from one or more data sources 114 and sort the information based on properties provided by one or more configuration files 302. It should be appreciated that various additional components have been omitted for clarity and conciseness, which may include various pre or post processing systems, data fetchers, network architecture, and/or the like. Furthermore, as noted, the data filer 124 may be incorporated within, or in communication with, one or more additional systems or sub-systems. Moreover, the data filer 124 may be a virtual representation that executes on one or more processors in accordance with different machine-readable instructions.

In this example, data sources 114, which as noted may be remote and/or on prem, may be streamed to the data filer 120. The data filer 124 may receive the information without physically moving the storage location for information within the data sources 114. Additionally, in this example, a configuration file 204 may provide instructions for how to file or sort the information from the data sources 114. For example, the configuration file 302 may include information regarding how to file or otherwise direct information. In one example, the information may include what type of information to identify within data from the data sources 114, an end location for the data, and/or the like. Configuration files 302 may differ based on different end applications. For example, configuration files 302 associated with tumor detection may identify data that includes images while configuration files 302 associated with co-morbidity information may identify data that includes particular text phrases. It should be appreciated that any number of configuration files 302 may be processed in parallel, or at least partially in parallel, and different pipelines or workflows may be established in accordance with these different configuration files 302.

Various embodiments provide for the data filter 124 to distribute or otherwise establish end connections, by itself or in part with other portions of the system, to different locations. For example, the data filer 124 may map identified and/or extracted data (either pre or post processing) to different locations, such as an AI/ML pipeline 304, an alert pipeline 306, a processing pipeline 308, and/or the like. As noted, different workflows may be defined that have different output pipelines and/or that include additional pipelines. Moreover, information may be fed to multiple pipelines at once. For example, the data filer 120 may provide information to the AI/MI pipeline 304 for use as input information for a compute job, to the alert pipeline 306 to provide clinical information to the user, and to the processing pipeline 308 for storage as training data to develop one or more additional pre-trained models. Furthermore, the data filer 124 may direct the information back to the data sources 114 for further storage. In this example, the AI/ML pipeline 304 may be associated with one or more workflows to map information to a particular compute instance(s) executing one or more pre-trained machine learning systems. The alert pipeline 306 may be used to provide information to practitioners for follow on actions. For example, if data includes information regarding treatment options for users, the information may be directed toward a practitioner that will carry out the treatment. Another example includes the processing pipeline 308, which may lead to further processing of the information, such as to extract additional data or the like. In this manner, the data filer 124 may be configured to process large quantities of data for mapping or otherwise directing to different endpoints based on configuration files without moving data from its original storage location.

FIG. 3B illustrates an example compute environment 320 that may be used with embodiments of the present disclosure. As noted, various components have been eliminated for simplicity and various pre and/or post processing tasks may be performed. For example, different processing steps may occur prior to using the queuing system 126.

In this example, the compute service 120 loads one or more pre-trained ML systems from the library 130. For example, the pre-trained ML systems may be trained on different types of data and then used with specific applications based on one or more configuration files 322, which may include additional training information, parameters associated with a trained ML system, and/or the like. As shown, the queuing system 126 may receive information from the data sources 114 (either processed data or pre-processed data) and then may map the data to particular portions of the compute service 120, such as to different layers of the trained ML systems, particular GPUs, and/or the like. As a result, data may be streamed to the compute service 120 as needed, rather than using wholesale data transfer techniques that may be time consuming and costly. Thereafter, one or more outputs 324 may be generated for use within a workflow, as noted herein.

FIG. 4A illustrates an environment 400 that incorporates a digital health data platform 402 that may be used to retrieve, evaluate, and transmit data from one or more data sources 114. The digital health data platform 402 may be integrated into existing services and storage solutions provided by health practitioners to leverage a large collection of information that may be stored using different standards and protocols but can, if properly evaluated, potentially provide useful health insights for a large number of patients. In this example, the data sources 114 may include remote and on-prem sources, as noted herein. For example, remote sources could be legacy databases or files stored in a cloud storage systems. Additionally, data sources 114 may include streaming data, such as information acquired from wearable devices that may be streamed intermittently or in real or near-real time (e.g., without substantial delay).

The illustrated digital health platform 402 may be part of a larger application environment 104 (FIG. 1) and/or offered within a service environment 404 associated with a provider, such as a health provider as a non-limiting example. In this example, the platform includes a data input system 406, such as the data loader 116, the labeling system 122, the data filter 124, the queue system 126, and/or the like. For example, the data input system 406 may be used for streaming and bulk loading of data to a cloud environment, among other options. Further illustrated is the event engine 204, which may be used to direct information received from the data sources 114, and also a storage location 408. The storage location 408 may be used to maintain standards or policies associated with the platform 402.

In at least one embodiment, the platform 402 is integrated within the service environment 404 to provide one or more additional services 410 and/or processing operations 412 to one or more users. For example, additional services 410 may include orchestration centers to manage workflows and communications, API management centers to enable development for individual groups, machine learning systems for classification and automation, an analytic engine to monitor usage and various metrics, compute services, and/or cloud storage services. Furthermore, processing operations 412 may include features such as data pre-processing, data post-processing, and the like. Accordingly, various outputs 414 may be generated. The outputs 414 may include information that is provided to a health practitioner, alarms, data that is added to another work flow, and/or the like.

Accordingly, various embodiment may implement a digital health data platform to address legacy data architectures that have not been maintained and/or have been insufficiently updated in accordance with modern business needs of data-driven organizations. In an example for healthcare practitioners, this could include using legacy coding information and/or identifying solutions for the sheer volume of data available within an organization. Various embodiments may build the platform on different stacks, which may include using features or services from one or more orchestration providers. In at least one embodiment, health data models, rooted in interoperability standards, may enable a variety of digital solutions (e.g., analytics, ML, etc.) with formal and automated data observability and reliability processes. Furthermore, event-driven architecture may be implemented to achieve real time or near real time (e.g., without significant delay) analytics and workflow orchestrated with integrated access to EHR and other systems of record. Furthermore, providing API management may enable plug-and-play integration to adapt to changes in the marketplace and adopt new solutions for data storage and transmission.

The data platform described herein may be useful as a standalone system or one that has been scaled to incorporate a variety of systems, such as numerous healthcare providers. Adding interoperability between providers may provide greater access to data and improved care. However, present systems provide barriers to entry, such as the cost of modernizing systems, data storage and transmission, and the like. Embodiments address and overcome these problems by leveraging universal system to receive, evaluation, and label information for use within one or more end systems, such as a compute service.

FIG. 4B illustrates an example implementation 420 of a data platform to process multimodal data to generate recommendations or health evaluations. In this example, the environment 104 receives information from the one or more data sources 114 for processing, evaluation, and the like from one or more components of the platform 402. For example, information may be acquired, evaluated, extracted, and then directed toward one or more machine learning systems based, at least in part, on instructions and/or a workflow associated with the application 110. Thereafter, different output 410 may be generated that may include research data, actionable findings, and the like.

As one non-limiting example of an application 110 that may be integrated into the environment 104 and/or used with the platform 402, a multimodal, longitudinal cardiovascular disease detection and risk prediction service may established. Cardiovascular disease is the number one cause of death in the US and disproportionately impacts patients from racial and ethnic minority groups and other vulnerable populations. Projects leveraging this application 110 may have the ability to directly impact clinical care for patients by enabling the timely identification of high-risk conditions and facilitating access to high quality, cardiovascular care and research.

Embodiments may integrate or incorporate multiple applications from one or more environment producers, such as stacks for data storage, deep learning, data lake services, analytics, and the like. The application 110 may enable generation of one or more workflows to enable ML algorithms to process real-time and/or near real-time cardiovascular data, thereby allowing clinicians to efficiently and effectively deliver evidenced-based, timely, and equitable care to patients with high-risk cardiovascular conditions. The application 110 may include a platform to leverage data to enable ML research and development of a cardiovascular care system. Inputs may be provided as multimodal data information to machine learning models for patients with heart failure. As non-limiting examples, information may include patent-reported outcomes, sensor data, wearable device data, curated lists of medications, patient lab work, electrocardiogram data, cardiac computerized tomography data, cardiac catheterization data, demographics, disease definitions, co-morbidities, interventions, testing, remedial actions and their results, pulmonary function tests, endomyocardial biopsies, cardiac magnet resonance imaging data, and/or the like. Various embodiments may leverage the rich data collected by various health services to facilitate opportunities to enhance patient care, improve access to treatment and clinical trials, and further research efforts. Furthermore, the application 110 may be scaled to various high value data types to provide additional data points to identify potential treatment options.

FIG. 5A illustrates an example process 500 for executing an operation using a compute instance. It should be understood that for this and other processes presented herein that there can be additional, fewer, or alternative operations performed in similar or alternative order, or at least partially in parallel, within the scope of various embodiments unless otherwise specifically stated. In this example, a remote data location is identified 502. The remote data location may refer to a storage location, which may be at a remote compute location and/or a cloud storage location, among various other options. Remote may also refer to one or more storage locations that are networked or otherwise not integral to one or more compute clusters or nodes that are executing different operations. In at least one embodiment, a remote data location is a location from which one or more network connects are used to transmit or otherwise access data stored therein. Stored data may be retrieved from the remote data location 504. Retrieval of the data may include transmission of at least a portion of the data over one or more data connections. It should be appreciated that various embodiments described herein are related to data streaming such that a physical location of the data is not modified or otherwise changed during operations. For example, the data may remain stored at the remote storage location with portions of it being transmitted or otherwise used for one or more compute operations.

In at least one embodiment, stored data is read 506 and one or more components from the stored data are extracted 508. The extracted data may be used to generate a new file and/or to generate a temporary file that may be used in one or more operations. Extracting information from the data may be based, at least in part, on one or more configuration files that may identify particular data types for later processing using one or more compute instances. For example, text may be extracted from a document, the text may be evaluated using one or more natural language processing systems, and then one or more phrases or groups of words may be extracted for further evaluation. It should be appreciated that only certain file within the data location may be evaluated based, at least in part, on different coding or identifying features. For example, files with a certain extension may be evaluated. The one or more components may be positioned within a queue 510. The extracted components themselves, a newly created file, or the original file with tags identifying the extracted components may be positioned within the queue 510.

In at least one embodiment, the one or more components are mapped to a compute instance 512. For example, rather than transmitting the data itself, storing the data locally, and then processing the data, mapping the one or more components may enable reduced bandwidth usage while still permitting meaningful evaluation of the data. The compute instance may then be used to execute one or more operations using the one or more components and a configuration file 514. The configuration file may include parameters for the one or more operations, which may be associated with one or more pre-trained machine learning models that use the parameters of the configuration file. In this manner, various embodiments enable streaming data compute execution.

FIG. 5B illustrates an example process 520 that may be used with embodiments of the present disclosure. In this example, a request to perform a compute operation is received 522. For example, a user may submit a request to a data platform and/or an automated workflow may generate a request to execute one or more compute operations. In at least one embodiment, a library of pre-trained models may be available within the data platform. A pre-trained model may be selected 524. The selection of the model may be based on the request. For example, a specific type of operation (e.g., identification) may lead to selection of a classifier. However, another type of operation (e.g., text extraction) may lead to identification of one or more natural language systems.

The pre-trained model may then be provided to a compute instance 526 and configured to execute an operation based on one or more configuration files 528. For example, the configuration files may include operational parameters for the pre-trained models based on the request. Remotely stored data may then be streamed to the compute instance 530 for execution of the compute operation 532. In this manner, a user or workflow may obtain a model, prepare the model for execution, and then perform a compute operation through one or more data platforms.

FIG. 5C illustrates an example process 540 to executing a workflow. In this example, a request to execute a workflow is received 542. For example, a digital health platform may receive the request from one or more authorized users, from a script scheduled to run a particular times, and/or the like. The workflow and/or the request may include information associated with different operations of the workflow. Based on this information, one or more pre-trained models and/or one or more data sources may be selected for the workflow 544. For example, the workflow may be directed toward a classification system that receives image information for processing via a trained machine learning system to classify anomalies within the images. Accordingly, one or more data sources may be selected along with one or more pre-trained classifiers.

In at least one embodiment, an execution mode for the workflow may be determined 546. The execution mode may be a determination as to whether the workflow facilitates compute services or labeling 548. If it is determined that a compute execution mode is selected, then one or more compute resources may be provisioned 550. For example, one or more nodes may be used to execute different compute operations, where the one or more nodes may be part of a distributed computing environment. In at least one embodiment, a data pipeline between the one or more data sources and the one or more compute resources is established 552. The data pipeline may enable transmission of information, or portions of information, that is mapped directly to one or more GPUs without intermediate transmission and/or storage. The pre-trained model may then be executed against the one or more data sources 554.

Alternatively, or in addition, a labeling execution mode may be selected where information from the one or more data sources is provided within an environment 556. The environment may also be part of a distributed computing service or may be loaded onto a device that made the request, among other options. The user may review the information and provide labeling information, which then received back at the system, such as the health platform 558. The labeling information may then be used to update training information for one or more pre-trained models 560, which may further be used to retrain one or more pre-trained models 562. In this manner, updated information may be acquired to continuously adjust and/or improve models. Furthermore, in at least one embodiment, the information may also be used to generate new models, which may be particularized for a specific use case.

FIG. 6 is a block diagram illustrating an exemplary computer system 600, which may be a system with interconnected devices and components, a system-on-a-chip (SOC), or some combination thereof formed with one or more processors. In at least one embodiment, the computer system 600 may include one or more processors 602 to employ execution units including logic to perform algorithms for processing data. The computer system 600 may form part of a compute cluster, for example within a data center, and may execute the instructions within one or more provisioned instances, such as a virtual machine.

Embodiments may be used in other devices such as handheld devices and embedded applications. Some examples of handheld devices include cellular phones, Internet Protocol devices, digital cameras, personal digital assistants ("PDAs"), and handheld PCs. In at least one embodiment, embedded applications may include a microcontroller, a digital signal processor ("DSP"), system on a chip, network computers ("NetPCs"), set-top boxes, gaming consoles, wearable devices, or any other system that may perform one or more instructions in accordance with at least one embodiment.

In at least one embodiment, the processor 602 may include various execution units to perform various applications, including machine learning or inferencing applications. Additionally, the processor 602 may be a single or multi-processor. The processor 602 may be coupled to a processor bus that may transmit data signals between processor 602 and other components in computer system 600. Further illustrated within the computer system 600 is a memory 604. In at least one embodiment, memory 604 may be implemented as a Dynamic Random Access Memory ("DRAM") device, a Static Random Access Memory ("SRAM") device, flash memory device, or other memory device. In at least one embodiment, memory 904 may store instruction and/or data represented by data signals that may be executed by processor 602. As noted, the memory may be any type of data storage device or non-transitory computer-readable storage media, such as a first data storage for program instructions for execution by the processor 602, a separate storage for images or data, a removable memory for sharing information with other devices, etc. The device may further include a display element 606, such as a touch screen or liquid crystal display (LCD), among various other options. As discussed, the computer system in many embodiments will include at least one input element 608 able to receive input from a user. This input can include, for example, a push button, touch pad, touch screen, wheel, joystick, keyboard, mouse, keypad, or any other such device or element whereby a user can input a command to the device. In some embodiments, however, such a device might not include any buttons at all, and might be controlled only through a combination of visual and audio commands, such that a user can control the device without having to be in contact with the device. For example, the input element 608 may be a component to receive signals received over a network. In some embodiments, the computer system includes one or more network interface or communication elements or components 610 for communicating over various networks, such as a Wi-Fi, Bluetooth, RF, wired, or wireless communication systems. The device in many embodiments can communicate with a network, such as the Internet, and may be able to communicate with other such devices.

Various embodiments can be described by the following clauses:

1. A computer-implemented method, comprising:
receiving a request to execute one or more compute operations against information within a remote data source;
identifying a location of the remote data source;
retrieving data stored within the remote data source;
extracting, from the data, one or more components;
queuing the one or more components;
mapping the one or more components to a compute instance; and
causing the compute instances to execute the one or more compute operations using at least the one or more components and a configuration file.

2. The computer-implemented method of clause 1, further comprising:
labeling the one or more components within the data in accordance with one or more data policies.

3. The computer-implemented method of clause 1, wherein the data is multi-modal data including one or more of text, images, audio, or video.

4. The computer-implemented method of clause 1, wherein data is maintained at the remote data source.

5. The computer-implemented method of clause 1, further comprising:
identifying, based at least in part on the one or more components, a pre-trained machine learning system; and
providing the pre-trained machine learning system to a compute instance associated with the one or more compute operations.

6. The computer-implemented method of clause 5, further comprising:
configuring one or more parameters of the pre-trained machine learning system based, at least in part, on the configuration file.

7. The computer-implemented method of clause 1, further comprising:
using a digital heath platform to receive the request, wherein the digital health platform is allowed to cause the compute instances to execute the operations.

8. A system, comprising:
one or more processing units to:
receive a request to perform a compute operation;
select, from a plurality of models, a pre-trained model based, at least in part, on the request;
provide, to a compute instance, the pre-trained model;
provide, to the compute instance, one or more configuration files having parameters for execution of the pre-trained model; and
cause remotely stored data to be streamed to the compute instance as an input to the pre-trained model.

9. The system of clause 8, wherein the one or more processing units are further to:
retrieve the remotely stored data; and
execute one or more pre-processing steps prior to transmission to the compute instance.

10. The system of clause 9, wherein the one or more pre-processing steps includes at least one of data modality recognition, labeling, or extraction.

11. The system of clause 8, wherein the remotely stored data is streamed to the compute instance absent an intermediate copying step to secondary storage.

12. The system of clause 8, wherein the one or more processing units are further to:
provide a landing page to a user associated with a health platform;
collect health data based, at least in part, on one or more parameters of the health platform; and
generate information indicative of diagnostic or treatment information for the health platform.

13. The system of clause 8, wherein the request is part of an integrated workflow associated with a multimodal diagnostic and evaluation system.

14. The system of clause 8, wherein the compute instance is dynamically selected based, at least in part, on the pre-trained model.

15. A computer-implemented method, comprising:
receiving a request to perform a compute operation;
selecting, from a plurality of models, a pre-trained model based, at least in part, on the request;
providing, to a compute instance, the pre-trained model;
providing, to the compute instance, one or more configuration files having parameters for execution of the pre-trained model; and
causing remotely stored data to be streamed to the compute instance as an input to the pre-trained model.

16. The computer-implemented method of clause 15, further comprising:
retrieving the remotely stored data; and
executing one or more pre-processing steps prior to transmission to the compute instance.

17. The computer-implemented method of clause 16, wherein the one or more pre-processing steps includes at least one of data modality recognition, labeling, or extraction.

18. The computer-implemented method of clause 15, wherein the remotely stored data is streamed to the compute instance absent an intermediate copying step to secondary storage.

19. The computer-implemented method of clause 15, wherein the request is part of an integrated workflow associated with a multimodal diagnostic and evaluation system.

20. The computer-implemented method of clause 15, wherein the compute instance is dynamically selected based, at least in part, on the pre-trained model.

Other variations are within spirit of present disclosure. Thus, while disclosed techniques are susceptible to various modifications and alternative constructions, certain illustrated embodiments thereof are shown in drawings and have been described above in detail. It should be understood, however, that there is no intention to limit disclosure to specific form or forms disclosed, but on contrary, intention is to cover all modifications, alternative constructions, and equivalents falling within spirit and scope of disclosure, as defined in appended claims.

Furthermore, although subject matter has been described in language specific to structural features and/or methodological acts, it is to be understood that subject matter claimed in appended claims is not necessarily limited to specific features or acts described. Rather, specific features and acts are disclosed as exemplary forms of implementing the claims.

17

What is claimed is:

1. A computer-implemented method, comprising:
receiving a request to execute one or more compute operations against information within a remote data source;
identifying a location of the remote data source;
retrieving data stored within the remote data source;
extracting, based on one or more processes corresponding to a format of the data, one or more components of the data associated with the one or more compute operations;
selecting, from a plurality of models, a pre-trained machine learning model based, at least in part, on the request;
providing, to a compute instance, the pre-trained machine learning model;
queuing the one or more components;
mapping, from a queuing location, the one or more components directly to a layer of the pre-trained machine learning model executing on the compute instance; and
causing the compute instances to execute the one or more compute operations using at least the one or more components and a configuration file, wherein the one or more components are streamed from the remote data source without locally copying the one or more components to the compute instance.

2. The computer-implemented method of claim 1, further comprising:
labeling the one or more components within the data in accordance with one or more data policies.

3. The computer-implemented method of claim 1, wherein the data is multi-modal data including one or more of text, images, audio, or video.

4. The computer-implemented method of claim 1, further comprising:
identifying, based at least in part on the one or more components, the pre-trained machine learning model.

5. The computer-implemented method of claim 4, further comprising:
configuring one or more parameters of the pre-trained machine learning model system based, at least in part, on the configuration file.

6. The computer-implemented method of claim 1, further comprising:
using a digital health platform to receive the request, wherein the digital health platform is allowed to cause the compute instances to execute the operations.

7. A system, comprising:
one or more processing units to:
receive a request to perform a compute operation associated with information stored in a remote data source;
extract, based on one or more processes corresponding to a format of data retrieved from the remote data source, one or more components of the data retrieved from the remote data source;
select, from a plurality of models, a pre-trained machine learning model based, at least in part, on the request;
provide, to a compute instance, the pre-trained machine learning model;
provide, to the compute instance, one or more configuration files having parameters for execution of the pre-trained machine learning model;
queue the one or more components;

map, from a queuing location, the one or more components directly to a layer of the pre-trained machine learning model; and
cause the pre-trained machine learning model to execute the compute operation using at least the one or more components and the one or more configuration files without copying the one or more components to the compute instance.

8. The system of claim 7, wherein the one or more processing units are further to:
execute one or more pre-processing steps on the data retrieved from the remote data source prior to transmission of the one or more components to the compute instance.

9. The system of claim 8, wherein the one or more pre-processing steps includes at least one of data modality recognition, labeling, or extraction.

10. The system of claim 7, wherein the data retrieved from the remote data source is streamed to the compute instance absent an intermediate copying step to secondary storage.

11. The system of claim 7, wherein the one or more processing units are further to:
provide a landing page to a user associated with a health platform;
collect health data based, at least in part, on one or more parameters of the health platform; and
generate information indicative of diagnostic or treatment information for the health platform.

12. The system of claim 7, wherein the request is part of an integrated workflow associated with a multimodal diagnostic and evaluation system.

13. The system of claim 7, wherein the compute instance is dynamically selected based, at least in part, on the pre-trained machine learning model.

14. A computer-implemented method, comprising:
receiving a request to perform a compute operation associated with information stored in a remote data source;
extracting, based on one or more processes corresponding to a format of data retrieved from the remote data source, one or more components of the data retrieved from the remote data source;
selecting, from a plurality of models, a pre-trained machine learning model based, at least in part, on the request;
providing, to a compute instance, the pre-trained machine learning model;
providing, to the compute instance, one or more configuration files having parameters for execution of the pre-trained machine learning model;
queuing the one or more components;
mapping, from a queuing location, the one or more components directly to a layer of the pre-trained machine learning model; and
causing the pre-trained machine learning model to execute the compute operation using at least the one or more components and the one or more configuration files without copying the one or more components to the compute instance.

15. The computer-implemented method of claim 14, further comprising:
executing one or more pre-processing steps on the data retrieved from the remote data source prior to transmission of the one or more components to the compute instance.

16. The computer-implemented method of claim 15, wherein the one or more pre-processing steps includes at least one of data modality recognition, labeling, or extraction.

17. The computer-implemented method of claim 14, wherein the data retrieved from the remote data source is streamed to the compute instance absent an intermediate copying step to secondary storage.

18. The computer-implemented method of claim 14, wherein the request is part of an integrated workflow associated with a multimodal diagnostic and evaluation system.

19. The computer-implemented method of claim 14, wherein the compute instance is dynamically selected based, at least in part, on the pre-trained machine learning model.

\* \* \* \* \*